(12) United States Patent
Selis

(10) Patent No.: US 7,670,350 B2
(45) Date of Patent: *Mar. 2, 2010

(54) BIOPSY DEVICES AND METHODS

(76) Inventor: James E. Selis, 167 Lake Park Dr., Birmingham, MI (US) 48009

( * ) Notice: Subject to any disclaimer, the term of this patent is extended or adjusted under 35 U.S.C. 154(b) by 635 days.

This patent is subject to a terminal disclaimer.

(21) Appl. No.: 10/631,204

(22) Filed: Jul. 31, 2003

(65) Prior Publication Data

US 2004/0097981 A1 May 20, 2004

Related U.S. Application Data

(60) Provisional application No. 60/400,113, filed on Aug. 1, 2002.

(51) Int. Cl.
*A61B 17/08* (2006.01)
(52) U.S. Cl. ...................... 606/151; 600/431
(58) Field of Classification Search ........... 606/151, 606/152, 153, 154, 155, 156, 157, 158; 600/431, 600/434
See application file for complete search history.

(56) References Cited

U.S. PATENT DOCUMENTS

| | | | |
|---|---|---|---|
| 5,441,487 A | 8/1995 | Vedder | |
| 5,526,822 A | 6/1996 | Burbank et al. | |
| 5,649,547 A | 7/1997 | Ritchart et al. | |
| 5,743,883 A | 4/1998 | Visconti | |
| 5,785,693 A | 7/1998 | Haining | |
| 5,853,366 A * | 12/1998 | Dowlatshahi | 600/434 |
| 5,893,856 A * | 4/1999 | Jacob et al. | 606/151 |
| 5,941,890 A | 8/1999 | Voegele et al. | |
| 6,056,700 A | 5/2000 | Burney et al. | |
| 6,063,062 A | 5/2000 | Paradis | |
| 6,113,611 A * | 9/2000 | Allen et al. | 606/151 |
| 6,161,034 A | 12/2000 | Burbank | |
| 6,181,960 B1 | 1/2001 | Jensen et al. | |
| 6,220,248 B1 * | 4/2001 | Voegele et al. | 128/898 |
| 6,228,055 B1 | 5/2001 | Foerster et al. | |
| 6,234,177 B1 * | 5/2001 | Barsch | 128/897 |
| 6,261,243 B1 | 7/2001 | Burney et al. | |
| 6,261,302 B1 | 7/2001 | Voegele et al. | |
| 6,347,241 B2 | 2/2002 | Burbank et al. | |

(Continued)

FOREIGN PATENT DOCUMENTS

WO    WO 9608208    3/1996

(Continued)

OTHER PUBLICATIONS

International Search Report dated Mar. 3, 2004. (PCT/US03/23995).

*Primary Examiner*—(Jackie) Tan-Uyen T. Ho
*Assistant Examiner*—Melanie Tyson
(74) *Attorney, Agent, or Firm*—Dobrusin & Thennisch PC

(57) ABSTRACT

An improved system for mammography analysis and methods of using the same. In one aspect, a clip comprises a first portion and at least one additional second portion connected to the first portion, the first and second portions adapted for elastic deformation for engaging tissue. In another aspect, an improved actuator for performing a breast biopsy is used to deploy a clip. In yet another aspect of the invention, there is contemplated a system for marking an evacuated breast cyst.

20 Claims, 7 Drawing Sheets

U.S. PATENT DOCUMENTS

| | | | |
|---|---|---|---|
| 6,356,782 B1 | 3/2002 | Sirimanne et al. | |
| 6,371,904 B1 * | 4/2002 | Sirimanne et al. | 600/3 |
| 6,425,903 B1 * | 7/2002 | Voegele | 606/151 |
| 6,549,800 B1 * | 4/2003 | Atalar et al. | 600/423 |
| 6,575,991 B1 | 6/2003 | Chesbrough et al. | |
| 6,605,047 B2 | 8/2003 | Zarins et al. | |
| 6,656,192 B2 | 12/2003 | Espositio et al. | |
| 6,662,041 B2 | 12/2003 | Burbank et al. | |
| 6,766,186 B1 * | 7/2004 | Hoyns et al. | 600/431 |
| 2001/0034528 A1 * | 10/2001 | Foerster et al. | 606/116 |
| 2002/0165561 A1 * | 11/2002 | Ainsworth et al. | 606/151 |
| 2003/0033006 A1 | 2/2003 | Phillips et al. | |
| 2004/0097981 A1 | 5/2004 | Selis | |

FOREIGN PATENT DOCUMENTS

| | | |
|---|---|---|
| WO | WO 00/07506 A2 * | 2/2000 |
| WO | WO 0024320 | 4/2000 |
| WO | WO 0024320 A1 * | 4/2000 |
| WO | WO 0067833 | 11/2000 |
| WO | WO 0067833 A1 * | 11/2000 |

\* cited by examiner

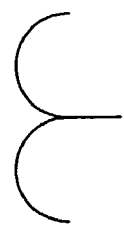 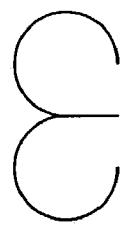 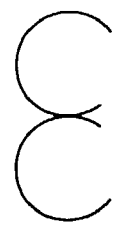
Fig-4A     Fig-4B     Fig-4C
 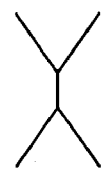 
Fig-4D     Fig-5A     Fig-5B
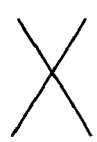  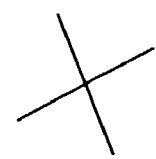
Fig-5C     Fig-6A     Fig-6B
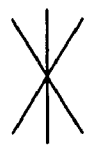     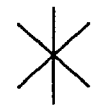
Fig-6C     Fig-6D

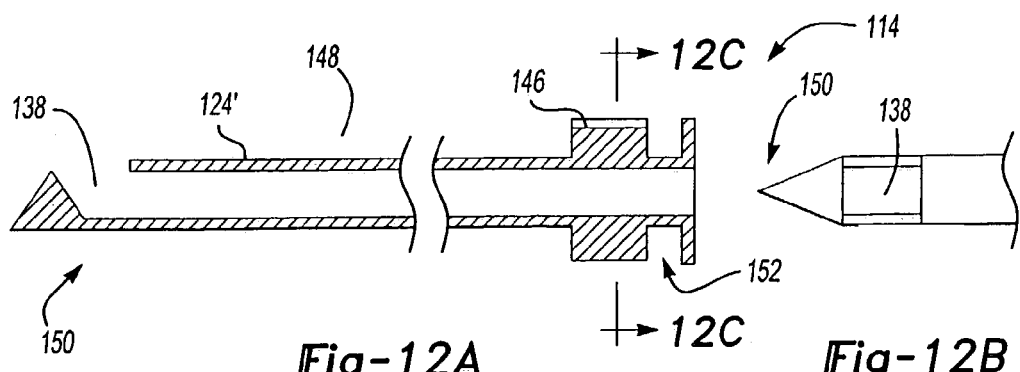
*Fig-12A*  *Fig-12B*
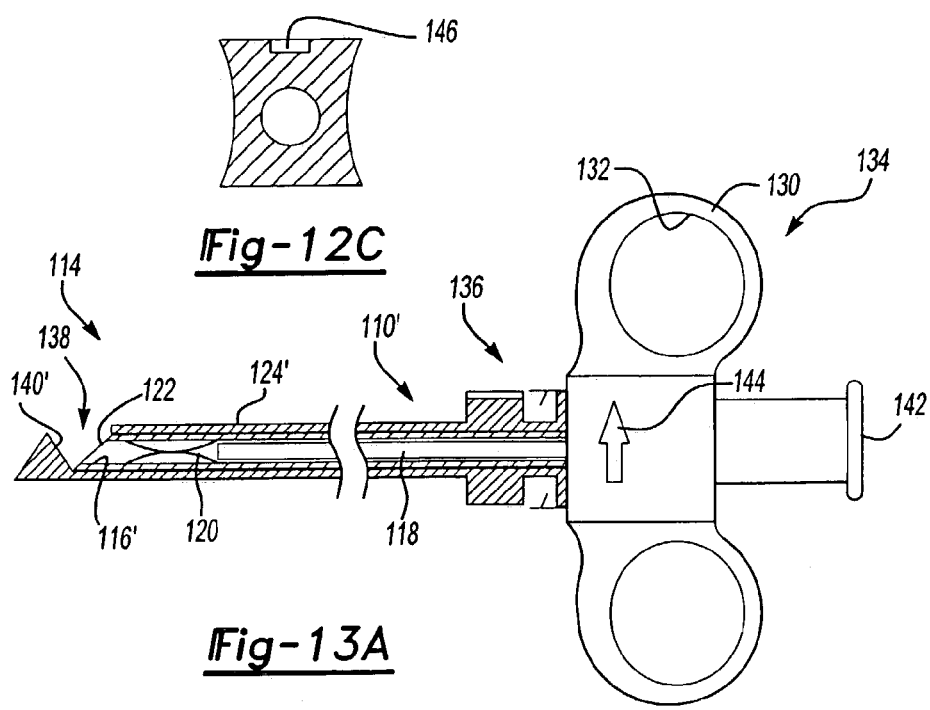
*Fig-12C*
*Fig-13A*
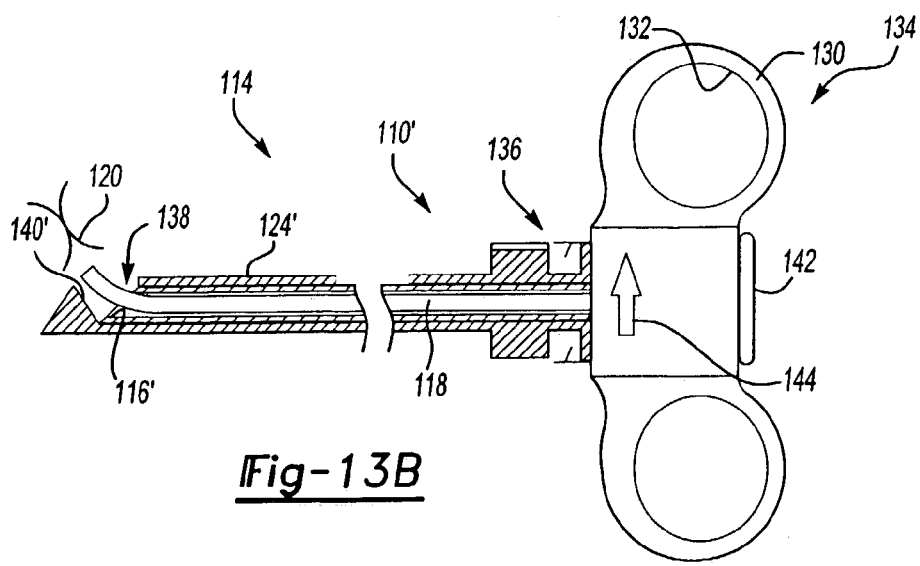
*Fig-13B*

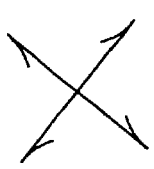   
Fig-16A     Fig-16B     Fig-16C     Fig-16D
 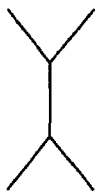 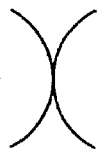 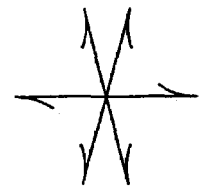
Fig-16E     Fig-16F     Fig-16G     Fig-16H
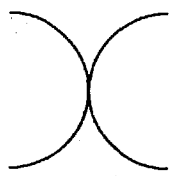 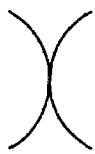  
Fig-16I     Fig-16J     Fig-16K     Fig-16L
  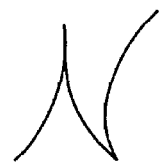
Fig-16M     Fig-16N     Fig-16O

BIOPSY DEVICES AND METHODS

CLAIM OF BENEFIT OF FILING DATE

The present application claims the benefit of the filing date of U.S. Provisional Application Ser. No. 60/400,113 (filed Aug. 1, 2002), the contents of which are hereby incorporated by reference in their entirety.

TECHNICAL FIELD

The present invention relates to devices and methods for performing biopsies, and more particularly to breast implantation clips for use as markers in mammography.

BACKGROUND

Percutaneous biopsy of the breast is a well-accepted alternative to open surgical biopsy with needle localization for those lesions seen by mammography or ultrasound but not able to be felt by the surgeon. When percutaneous biopsy is performed, it is frequently necessary to place a metal clip at the site of biopsy. This is done for several reasons. For example, the lesion biopsied might be partially or entirely removed. If the lesion is proven to be malignant, it is necessary to subsequently do a wide excisional biopsy after needle localization to remove any residual malignancy. The clip makes the site of biopsy apparent, assuring accurate localization. In addition, if something is seen on both mammography and ultrasound, it is not always certain that the lesions are one and the same. A biopsy under ultrasound guidance with placement of a clip allows confirmation by mammography that the lesion is the same or different than the one seen on the mammogram. Further, the presence of a clip seen on a mammogram alerts the radiologist that a biopsy has been performed, prompting the radiologist to more closely evaluate the site of biopsy.

The vast majority of percutaneous breast biopsies are performed under art-disclosed stereotactic guidance techniques, and generally use a device known as the Mammotome® (by Johnson & Johnson) (e.g. biopsy or tissue removal device). The clip that is employed is generally prone to pinching a minute amount of breast tissue. Sometimes, the clip may fail to hold onto the tissue or the clip may migrate to a different undesired location.

U.S. Surgical has produced a clip from a wire with a memory that is delivered into the breast and forms a ring. It is larger in diameter than the Mammotome® device clip and can grab significantly more tissue. The clip is an alloy containing nickel. Recent indications are that U.S. Surgical may no longer manufacture this clip, thus creating a potential supply issue for existing users.

SenoRx, Inc. produces metal markers embedded in Gelfoam pellets (a product that promotes clotting of blood), called Gel Mark™. The product is packaged to include a plurality of pellets and one radiographic marker. The pellets, however, potentially result in undesired migration of particles.

Although there is current production of a hand-held Mammotome® device, for the purpose of ultrasound guided biopsy, for some users this device may be awkward and cumbersome to use. The majority of ultrasound-guided biopsies are done with use of Tru-cut needles. This can be done through a coaxial needle. A Bard 12 gauge biopsy needle could be used through an 11 gauge coaxial needle. Through this 11 gauge coaxial needle, a U.S. Surgical clip might also be delivered, although U.S. Surgical is not believed to have marketed their clip for use during ultrasound-guided biopsies.

Another product is manufactured by Inrad. This clip is used for placement during ultrasound-guided biopsy because the delivery device is steel and does not provide the flexibility necessary for delivery through the Mammotome® needle. This delivery device has a beveled tip, allowing advancement through breast tissue without a coaxial needle.

Breast biopsies using an 11 gauge coaxial needle have been performed. However, most biopsies are typically done using smaller needles, e.g. a 14 gauge biopsy needle with 13.5 gauge coaxial needle. Such small sizes, in many environments, however, are believed to be too small to efficiently allow advancement of the delivery device of current commercially available clips.

Turning to another consideration, when a cyst in the breast is aspirated, a spectrum of different types of fluid can be recovered. These might range in color from white to yellow to green or brown. They may be mucousy or bloody and thus can be thick or thin. Some physicians send all samples for cytology analysis, while other physicians may send only grossly suspicious samples (e.g. mucousy or bloody). Regardless of which cyst fluids are sent for cytology, once a cyst is evacuated or in the event that a cyst cannot be fully evacuated because it contains a solid component, a radiologist would like to place a clip into the lesion. It is often important to mark the cyst so that should the cytology prove malignant, or otherwise require further attention, the exact site of the lesion would be known and a needle localization could be subsequently performed.

There is a need for improved devices for breast biopsy, cyst aspiration or both, to overcome the above-discussed disadvantages of current commercial products.

The following United States patents are also useful to more fully understand the context and application of the present invention and are all hereby expressly incorporated by reference herein: U.S. Pat. Nos. 6,161,034; 5,526,822; and 5,649,547. Devices disclosed in the above patents may be modified as desired to incorporate the inventive features disclosed herein.

SUMMARY OF THE INVENTION

In one aspect, the present invention meets the above needs by providing an improved clip for mammography analysis, comprising a first portion that is straight, arcuate or a combination thereof; and at least a second portion that is straight, arcuate or a combination thereof, and which is connected to the first arcuate portion at an apex, wherein the first and second portions are adapted to be compressed to fit within a tube of a delivery device and to elastically deform relative to each other upon exiting the tube for engaging tissue.

In another aspect the present invention contemplates an improved device, preferably of compact design, for performing a breast biopsy, marking an aspirated cyst, or both, comprising a gripping portion including finger rests attached to a hub portion; a tube having defined at one end portion a hole; and a driver having an actuator member in driving relation therewith; wherein upon translation of the actuator member the driver advances in the tube to advance any clip located in the tube for expulsion through hole, and further wherein the actuator requires only one hand to deploy the clip from the clip delivery portion and is substantially free of a lock that requires unlocking to permit the actuator to operate.

In yet another aspect of the invention, there is contemplated a device and a method for marking an evacuated cyst, such as a breast cyst, comprising the steps of inserting a needle into a fluid filled cyst (e.g. a breast cyst); removing fluid from the cyst for collapsing the walls of the cyst; and inserting a clip as a marker into the cyst using the needle.

DESCRIPTION OF THE DRAWINGS

FIGS. 4A-4D, illustrate alternative configurations for clips of the present invention in their deployed state.

FIG. 5A illustrates an alternative configuration for a clip of the present invention in its deployed state.

FIG. 5B is an end view of the clip of FIG. 5A.

FIG. 5C is an example of an alternative end view of a clip of FIG. 5, in which the ends are rotated relative to each other for achieving a three dimensional configuration in a deployed state.

FIGS. 6A-6D illustrate alternative configurations for clips of the present invention in their deployed state.

FIG. 12A is a side section view of another alternative device to illustrate a preferred breast cyst aspiration needle device.

FIG. 12B is a top plan view of an end portion of the embodiment of FIG. 12.

FIG. 12C is a sectional view taken through lines 12C-12C of FIG. 12A.

FIGS. 13A and 13B illustrate a side section view of another alternative device to illustrate a preferred cyst aspiration needle device with a side hole in combination with a coaxially inserted clip delivery device.

FIGS. 16A-O illustrate yet further examples of alternative clips in accordance with the present invention.

DETAILED DESCRIPTION OF THE PREFERRED EMBODIMENT

Figure 1:
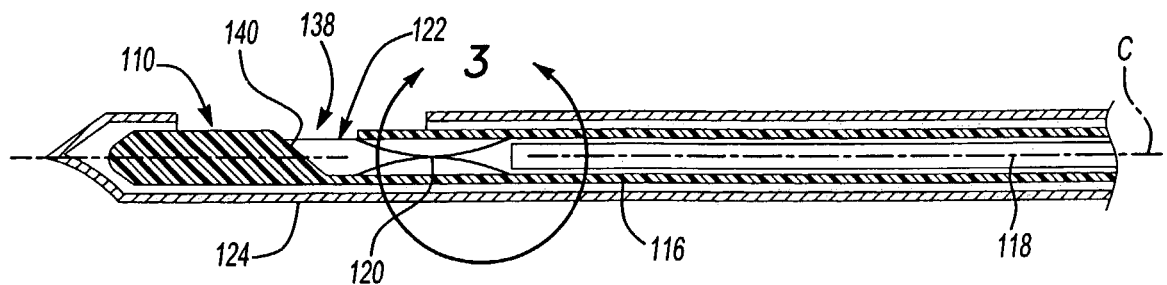
FIG. 1 illustrates a side view of an illustrative system which is suitable for use to deploy clips in accordance with the present invention including a clip delivery device in combination with a biopsy instrument.

The present invention is directed to improved devices and methods for medical diagnosis and treatment, and particularly devices that are employed for mammographic analysis, such as for the detection and treatment of cancerous or other abnormal growths. The present invention contemplates an improved clip, such as for use as a marker, a delivery device for deploying the clip, a cyst aspiration device, combinations thereof and methods of using the same.

As will be seen from the description that follows, the various inventive features are not confined to a single application, but rather are capable of numerous variations. Accordingly, though described in a certain context, as will be apparent, features may be interchangeable among embodiments. For sake of brevity, while still providing ample instruction to the skilled artisan, the features herein are described without limitation in embodiments featuring the employment of a clip delivery device 110 (110') by itself, with a biopsy instrument 112, such as a vacuum assisted instrument or a cyst aspiration device 114 (114') or combinations thereof. Accordingly, it is contemplated that the clip delivery device may deploy a clip through an end hole or a side hole of a rigid, semi-rigid or flexible tube, and possibly thereafter through an end hole or a side hole of an outer needle (which itself may be a part of an integrated or separately connectable device and may be rigid, semi-rigid or flexible).

In general, one common feature of a number of the different embodiments herein is the use to precisely deploy clips directly at a biopsy site, the site of an aspirated cyst, or any other desired site, and thus be able to accurately and reliably mark the site with the clip, as will be demnonstrated by the various embodiments herein, and particularly taking into account the alternative clip designs of FIGS. 4A-4D, 5A-5C, 6A-6D and 16A-16O.

As seen from those drawings the clips typically are a relatively fine structure, and are contemplated as commonly being made of a wire, such as a surgical stainless steel wire, a titanium wire, nickel containing metals, a biocompatible polymer or the like. Of course, other biocompatible materials may likewise be employed, such as, other non-corrosive materials or otherwise.

In one aspect of the present invention, the clip may be delivered through a system or according to a method that uses a biopsy instrument such as a Mammotome® vacuum-assisted biopsy instrument, available through Johnson & Johnson, pursuant to which a tissue sample may be obtained with a needle by applying a slight vacuum for drawing, cutting and/or removing tissue.

In general, any delivery device may be used, whether employed in combination with a suitable biopsy instrument or not. For example, a device might be employed in which a tissue sample is obtained with a needle in combination with a spring loaded mechanism to cut and remove tissue. The clip might also be delivered during open surgery. Preferably any device may be employed for performing mammographic analysis provided it is suitable for stereotactic techniques, ultrasound techniques or a combination thereof.

It is contemplated that the delivery device includes an actuator portion that may be removably associated with the delivery device, the biopsy instrument or both. Thus, for example, one preferred apparatus may include a biopsy instrument that includes a needle portion that is insertable into a patient. Coupled with or within the needle portion, or integrally defined as part of the needle portion may be a cutter (e.g., a movable needle that can be manually driven, driven by a motor, or both), a vacuum device or a combination thereof.

In some embodiments, accordingly, the delivery device of the present invention is flexible over at least a portion of its length to provide better maneuverability through a tissue mass or otherwise. Therefore, it is foreseeable that at least a portion of the delivery device is made of plastic or another flexible material. However, the present invention also contemplates the use of a rigid delivery device comprising a harder material such as a rigid plastic, metal or otherwise. Combinations of different materials may, of course, be employed as desired.

Figure 10:
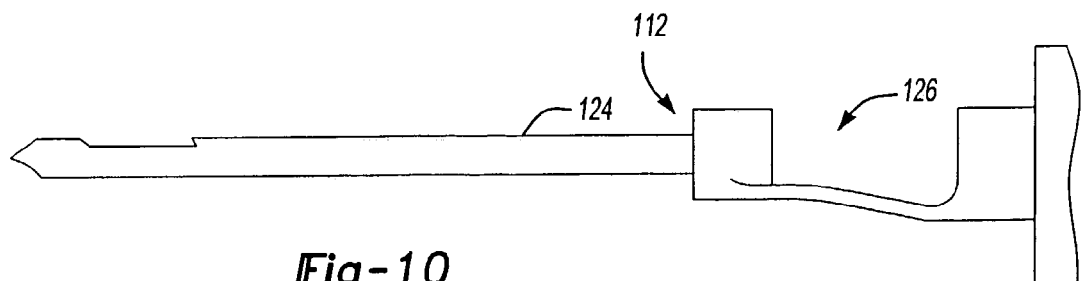
FIGS. 10, 11A and 11B illustrate a plan view of a biopsy instrument useful in combination with a clip delivery device of the present invention.
Figure 11A:
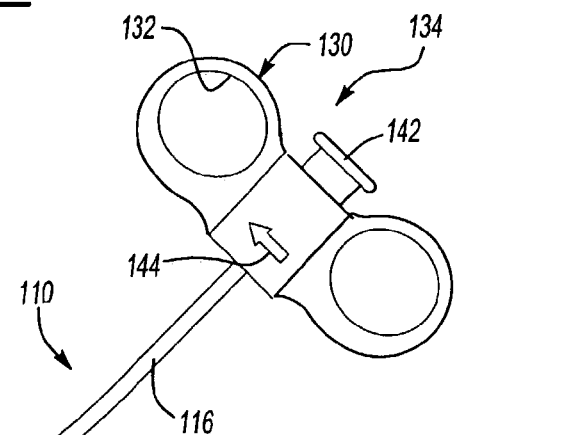
Figure 11B:
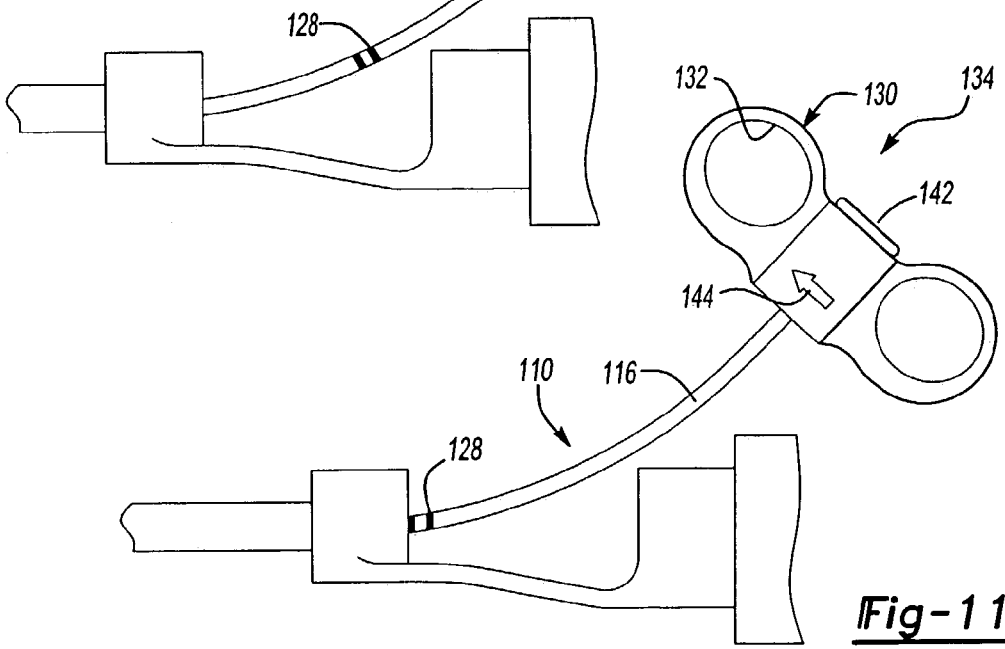
Figure 11C:
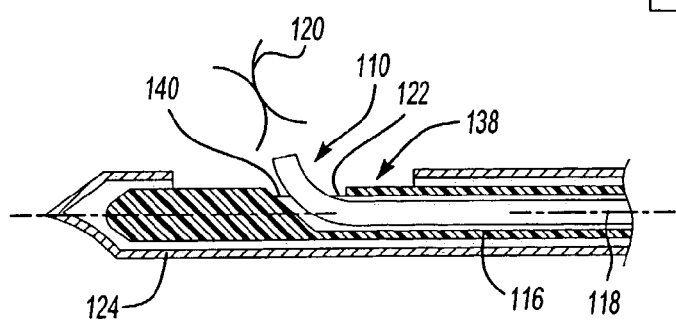
FIG. 11C illustrates a side section view of a biopsy instrument of FIGS. 10, 11A and 11B.

Referring to FIG. 1, one example of a system is illustrated as comprising a clip delivery device 110 that includes a delivery tube 116 (which optionally may be open, such as by a longitudinal groove, notch, slot or aperture at an end or over at least a portion of its length, and is illustrated as having a blunt tip and a side hole) and a driver 118. A portion of the driver 118 is configured to slide within the delivery tube 116 and push an object, such as a clip 120 (shown in an undeployed state) or otherwise out of a tube exit opening 122. As shown in FIG. 1, the system includes a portion of a biopsy instrument, particularly one including a needle 124. Referring also to FIGS. 10, 11A and 11B, one such biopsy instrument 112 may include a window portion 126 into which the delivery tube 116 of the clip delivery device 110 can be axially inserted, such as to a predetermined location as suitably defined by a visual indicator 128.

Referring again to FIGS. 10, 11A and 11B, preferably, the clip delivery device 110 further comprises a gripping portion 130 having a finger rest 132 and a hub portion 134 affixed, integrated with or otherwise attached to the tube, driver or both. The gripping portion may be enclosed as shown, or it may be open. It may be adapted for receiving a single finger or a plurality of fingers.

As seen, advantageously, the clip delivery device 110 (110') may further comprise or be integrated or used with an aspiration needle device, which may be open at an end or over at least a portion of its length. The aspiration needle device may comprise a separable unit configured to temporarily receive the tube 116 (116') of the device 110 (110'), or alternatively, the aspiration needle device, the tube 116 (116'), or both may be formed with, permanently or temporarily attached to a portion of the delivery device 110 (110').

For example, one such suitable attachment feature might include a luer lock or other suitable attachment mechanism, which would permit a user to readily assemble or disassemble components. For example, without limitation, as depicted more particularly in FIGS. 12A-12C and 13A and 13B, it is contemplated that a connecting portion 152 connects the needle or device to a luer lock connector 136 associated with the clip delivery device 110'. See also FIG. 15. The needle, the tube or both may be connected with such an attachment mechanism.

Alternatively, the aspiration needle device 114 (114'), tube 116 or both may be affixed to the delivery device 110' using an adhesive, through welding (e.g., friction welding), integrally formed or otherwise. Preferably, when combined together (as seen alternatively, for instance, in the various embodiments of FIGS. 1, 3 11A-11C, 13A, 13B, 14 and 15), the needle 124 (124') and the tube 116 will be coaxially aligned about a center line such as center line "C". The coaxially alignment may be created using the attachment device for the needle (e.g., luer lock or otherwise) or it may be created other structural alignment features such as a mating configuration between the end portions of the needle and the tube. Such a needle would typically be configured with a needle opening 138, an open end or otherwise so that any needle opening would be aligned with the tube opening 122, as in FIG. 1. With the addition of a needle 124 to the delivery device 110, it is possible to perform additional functions such as excise, aspirate or otherwise manipulate a portion of a tissue sample.

In any of the examples contained herein, it is foreseeable that a clip 120 is compressed upon itself and inserted into the tube portion 116 (116') of the delivery device 110 (110') at some point prior to the use of the same. As such, the clip may be inserted into the tube at any time from the manufacture of the tube or up until just prior to the use of the delivery device. It is further contemplated that the clip may comprise a separately manufactured component, as described in greater detail herein, or it may be a removable portion of the delivery tube or any other portion of the delivery device.

Also, it is contemplated that more than one clip may be loaded within a single delivery device. For example, the delivery device may be configured with a plurality of clips compressed upon themselves and located within the delivery tube, needle, or otherwise. As such, it would be possible to insert more than one clip into a breast, either at similar or different locations, using a single delivery device.

As can be appreciated, the device 110 is inserted into a tissue sample, such as a breast or otherwise, and the end portion including the tube 116, the needle 124 or both, is positioned to the portion of the tissue that is of interest. Once positioned, manipulation of the tissue may be performed by, for example, providing a vacuum through a portion of the needle 124', tube 116' or otherwise, to pull the tissue into the needle opening 138. Advantageously, the vacuum force may be used to assist in excising a portion of the tissue for pathological analysis or otherwise. It should be appreciated that in addition to the above described structure any suitable additional blade configuration may also be employed.

Either before or after the excising or aspiration of the tissue, a clip 120 may be deployed through the tube opening 122 and needle opening 138, if present. The device and/or needle may then be rotated (e.g., from about 90 to about 270°, and more preferably about 180°) so when it is withdrawn, the needle opening 138 does not hook or otherwise catch onto the clip 120 and accidentally dislodge it.

In certain embodiments, such as shown in FIGS. 1 and 11-13, the delivery tube, the needle or both has a guide surface such as a ramp 140 (140') on the inside that directs the clip 120 out of the tube opening. However, alternatively the delivery device may comprise a rigid or semi-rigid tube having a tube opening directly defining the axial end of the tube, for delivery of a clip. With this alternate configuration, it is foreseeable that the tube is shaped or comprises needle-like characteristics for allowing the insertion directly into tissue.

Figure 3:
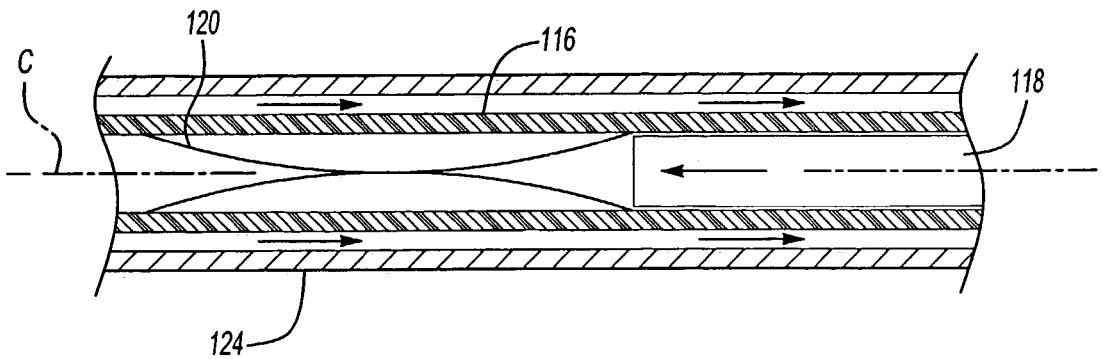
FIG. 3 illustrates an enlarged section of FIG. 1 showing deployment of a clip of the present invention through a deployment tube of a clip delivery device within a biopsy instrument.
Figure 7:
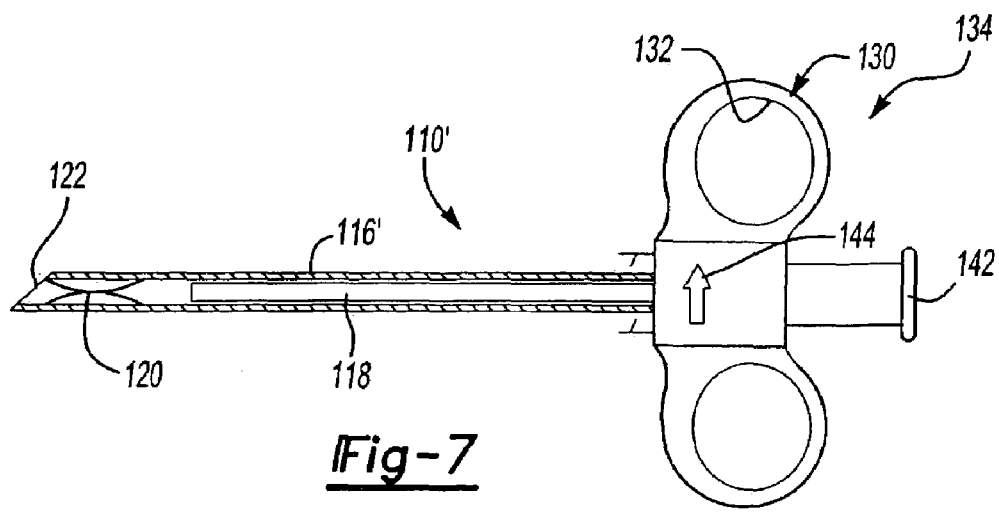
FIGS. 7-8 illustrate a rigid shafted clip delivery device respectively in pre- and post-deployment states.
Figure 8:
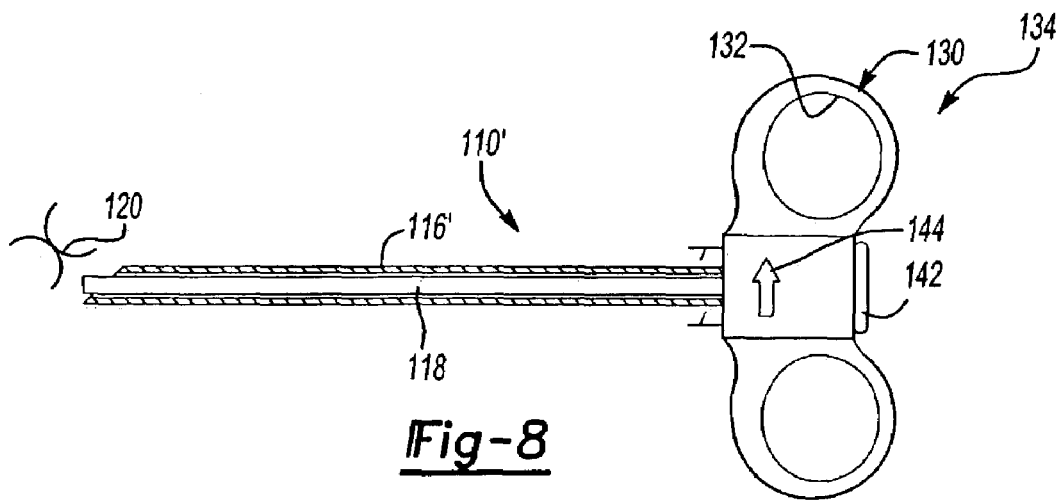
Figure 9:
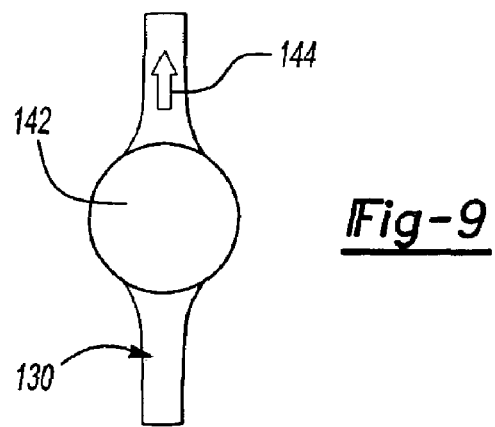
FIG. 9 is an end view of the device of FIGS. 7 and 8.
Figure 15:
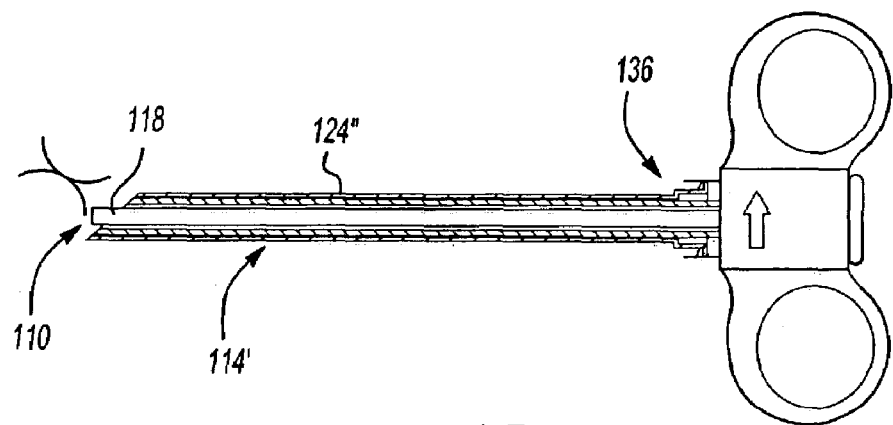
FIG. 15 is an example of clip delivery device employed in combination with an aspiration needle as in FIG. 14.

As best seen in FIGS. 1, 3 and 11 (with reference to clip deployment with a biopsy instrument having a needle 124, such as a vacuum assisted biopsy instrument), FIGS. 7 and 8 (with reference to clip deployment independent of an additional biopsy instrument), and FIGS. 13A, 13B and 15 (with reference to clip deployment in combination with a cyst aspiration needle device), the deployment of the clip comprises advancing (e.g., by sliding) the clip within the tube using a suitable driver 118. To fully deploy the clip within the tissue of interest, the driver extends to the end of the tube and, if desired, then through tube opening and any needle opening, if present. This ensures that the clip 120 is free from both the delivery device and the needle 124 (124') prior to withdrawal or rotation. Though the driver 118 is applying a force to advance the clip within the tube, in a highly preferred embodiment, it should be appreciated that it does not impart any significant force to the clip to cause the clip to elastically deform about itself upon exiting the delivery device.

The driver 118 may be solid along its length, or at least partially hollow. As such, it is foreseeable that the channel within the drives may be used to provide a path for fluid, instruments or otherwise. It may be coated or uncoated. For example, it may have a low friction material over an outer surface.

In one embodiment (e.g., as shown in FIGS. 7 and 8), for the clip 120 to be delivered under ultrasound-guidance (e.g. employing a suitable ultrasound instrument), it is advantageous for the delivery device 110' to include a rigid tube 116 (e.g., made of a steel) and the tip to be beveled.

One benefit of the present invention is that clip deployment can be accomplished with or without a vacuum assist. Precise location of a clip relative to the biopsied region is possible, and it is also possible that the clip can be deployed to the exact location of the biopsy.

It will be appreciated that, particularly for mammographic analysis, the area biopsied can sometimes be very small. Also, after biopsying a lesion, the lesion potentially might become obscured by bleeding. As such, it may be desirable for the coaxial needle 124 (124') to be at least temporarily left in place so that it serves as a valuable landmark for the accurate placement of the clip 120. Thus the present invention contemplates a step of temporarily placing a needle (e.g., a 13 gauge needle or another needle, preferably open at both ends) in the biopsy region prior to deployment of a clip. Thereafter, the tube of the delivery device is inserted into the needle for deployment of the clip.

Though preferred delivery devices are disclosed herein, such disclosure is not intended to foreclose the adaptation and use of other devices. Additional examples of delivery devices for use herein are described without limitation in U.S. Pat. Nos. 5,526,822; and 5,649,547, hereby incorporated by reference.

Figure 2A:
FIGS. 2A-2C illustrate prior alternative configurations for clips.
Figure 2B:
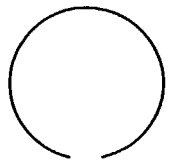
Figure 2C:

The design of the clips 120 helps to avoid the possibility of migration. That is upon deployment, the ends of the one or plurality of wires are such that they catch and attach to the tissue, such as by unfolding upon itself (e.g., by rotating at least 45° relative to an opposing portion, such as about its apex, more preferably at least 60°, still more preferably greater than 90°, and possibly greater than 180°), and employing its intrinsic elasticity to force an end of the clip into the tissue. Preferably the stored energy of a clip as it resides (e.g., in a compressed state relative to its relaxed state) within the clip delivery device prior to deployment is sufficient that it can unfold upon itself and penetrate tissue in the absence of an externally applied force, as is common with prior clip devices, such as FIG. 2A (which generally employs a detachable tensioning wire). Nonetheless, the shape of the clip is such that uncontrollable spiraling, which might lead to undesired migration can be avoided.

Accordingly, as the wire of the clip progresses to its relaxed state, upon exiting the delivery device 110, it is capable of pulling the clip 120 by itself (i.e., under its own stored energy and preferably in the absence of additional user-applied energy) into position, assuring secure deployment and substantially preventing migration.

Various examples of clips 120 useful in accordance with the present invention are shown, without limitation, in FIGS. 4A-6D and FIGS. 16A-16O.

In one set of examples of a preferred clip 120, arcuate portions (e.g. FIGS. 4A-D, 6A, 16C, 16D, 16G, 16I, 16J and 16O) may be joined at an apex, or a plurality of apexes, to form a clip of the present invention. Alternatively, in another set of examples of a preferred clip, the clip 120 of the present invention may include straight portions (e.g. FIGS. 5A, 6B-D, 16A, 16B, 16E, 16F, 16H and 16K-N) joined at an apex or a plurality of apexes. It is further contemplated that any of the above clip examples may be combined with any other clips, or the same clip, to form yet more examples of a clip 120 of the present invention. Furthermore, all of the above clips 120 may further comprise additional features, which may be resistant to migration through a breast, such as a barb as in FIGS. 16A-E and 16H, 16K and 16L.

In another aspect of the present invention, a preferred delivery device 110 of the present invention comprises an actuator 142 as seen in FIGS. 7, 8, 11A, 11B, 13A and 13B, which is compact in design and is useful by itself or in combination with another biopsy instrument such as has been described for performing either or both of the percutaneous or ultrasound guidance techniques. A preferred driver 118 comprises a pushrod or piston like configuration, wherein the actuator 142 applies a force to one end thereby driving the piston or pushrod through the tube along with any clip contained therein. However other driver and actuator configurations are available and contemplated, as well known in the art of tissue aspiration and excising.

Advantageously, the design of a preferred gripping portion 130 (e.g., handle, or otherwise) and deployment actuator 142 of the present invention requires only one hand, either left or right (e.g. the devices are designed for ambidextrous use), to deploy the clip 120. Further, though a lock may be employed, a preferred delivery device 110 (110') has no lock that requires unlocking. Instead, there may be incorporated some slackness or other approach for providing initial "play" when actuating the actuator 142 (such as by pressing a button, squeezing a trigger or the like) before which the clip is deployed. This can be accomplished with a suitable driver, for example, with a suitable cable, or more preferably by a push rod (e.g., having a length that is slightly shorter than the shaft in which it is disposed). In this manner it is possible to gain further control to help avoid accidental deployment of the clip.

As illustrated in the embodiments of FIGS. 8-12, a preferred gripping portion 130 will have a suitable grip portion, such as one that has finger rests 132 (e.g., at least one and preferably two opposing open or generally semicircular finger grips or substantially entirely enclosed circular finger grips) that help secure control, for either left or right-handed operators. As seen, for example in FIGS. 7, 8, 11A, 11B, 13A, 13B and 15, in one preferred approach for the device, the gripping portion 130 optionally may be configured with a surface marking 144 (e.g., an arrow, text, or otherwise) pointing toward the direction of the tube opening or needle opening, indicating the direction in which a clip will be deployed from the device.

Additionally locator features may also be employed. For example, as shown in FIGS. 12A-13B, a notch 146 might be employed to help align the gripping portion with a needle or other component that is separably attached, such as by way of a luer lock.

FIGS. 7 and 8, and FIGS. 13A and 13B illustrate side views of an example of a preferred gripping portion 130 and deployment actuator 142 of the present invention, shown in illustrative pre-deployed (FIGS. 7 and 13A) and deployed (FIGS. 8 and 13B) conditions.

Once the button of the actuator 142 is depressed completely and the clip 120 has been fully deployed, the button of the actuator may include a feature for automatically locking it into a depressed position, providing feedback to the physician that the clip has been fully deployed. For example, a detent, an over center lock, a snap, or the like locking mechanism, might be employed in the gripping portion which is engaged only upon deployment. Upon locking of the locking mechanism, there is an audible sound and/or just prior to locking there is slight increased resistance, which must be overcome, providing palpable feedback that the clip has been fully deployed.

The actuator 142 may further comprise a return device (not shown) for retracting the end portion of the driver back within the tube. As such, a return device (e.g., a spring or otherwise) may bias the movement of the actuator 142 so that upon release of the same the actuator will retract to predetermined position (e.g., a stop position, a lock portion, an indentation or projection, the original position or otherwise). By retracting the driver into the tube, the clip will be substantially free from the device and will not catch or otherwise be dislodged from the insert position during rotation or withdrawal of the needle from the object into which it is inserted.

The tube and/or needle associated with any delivery device herein may employ a flexible shaft or a rigid shaft or a combination thereof. It may be made of a suitable metal (e.g., surgical steel, titanium or the like), plastic or other material. It may be coated or uncoated, transparent, opaque or combinations thereof.

The actuator of the present invention may optionally include a hub portion that is adapted for temporary or permanent connection with a shaft, tube or the like. For example, as seen in FIG. 15, a fitting 136 (e.g., a Luer lock fitting) is provided for attachment of a needle or other projection with the hub portion of the actuator.

Figure 14:
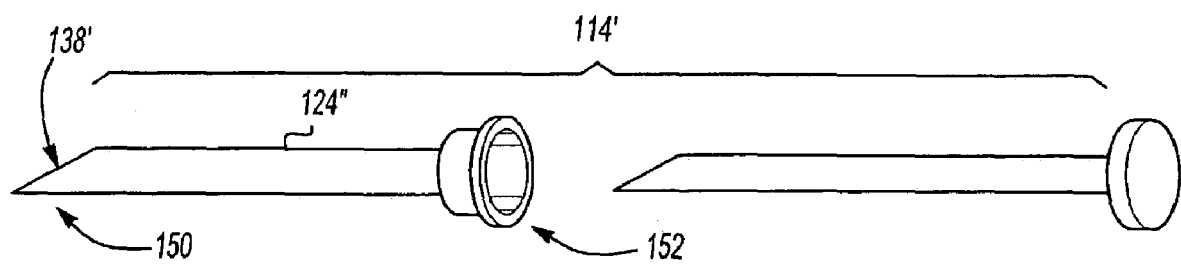
FIG. 14 is an example of an alternative cyst aspiration needle with an end hole.

With reference now to FIGS. 12A-15, there are shown alternative embodiments contemplated within the present invention, in which a cyst aspiration device 114 (114') is employed, and preferably one through which a clip 120 could be deployed. Examples of needles 124' (124") are shown in FIGS. 12A-12C, 13A, 13B, 14 and 15. For instance, the needle preferably includes a shaft 148 (e.g., metal such as steel or titanium, plastic or the like), with a cutting portion 150 (e.g., having a tapered tip) and a connecting portion 152. Though an end hole 138' may be employed (as seen in FIGS. 14 and 15), the cutting portion 150 in FIGS. 12A-13B is preferably configured with a side hole 138 that will align with a fixed or displaceable cutting edge (e.g., a bevel on a stylet). Thus, a stylet or other device may also be employed for cutting tissue, preventing tissue from filling the needle before aspirating a cyst, or both.

As seen, the use of a typical Luer lock 136 or other suitable end fitting at the connecting portion preferably allows ease of use with readily available syringes or with an actuator 142 such as described in the above (e.g., with or without finger holes) for delivering a clip 120. It also allows for removal of the actuator 142 while retaining a needle in place. Thus it is possible that a clip is loaded into the device after the needle is inserted into the patient.

The gauge of any aspiration needle 124' (124") of the present invention may be substantially the same as or larger than the gauge of conventional needles available for cyst aspiration, it being recognized that frequently the fluid is thick and will not be able to be practically withdrawn through a typical 19-gauge needle, in the absence of a thinning protocol (which might be employed, such as by chemistry, thermally, or otherwise). A larger gauge, e.g., about 15 to about 18 gauge is preferred in one particular embodiment for evacuating cysts.

Also, the needle lengths of the present invention may vary as well. For example, the needle may be configured having a length from about 1 cm to about 10 cm and, in one embodiment, more preferably about 2 to about 5 cm; and more preferably about 5 to 10 cm in another embodiment.

At times, having a needle with a long length can prove to be an advantage. For example, cysts are sometimes deeper than can be reached with a 2-cm blood-drawing needle. As such, the needle of the present invention would be produced in one or more lengths and gauges that would precisely match the steel shafted breast marking clip device. The length or gauge of the needle could be unusual, but matched to the length of the steel deployment device so that other commercially available needles controllably may be used with it, such as with an adapter, the providing of such an adapter also being contemplated as within the scope of the present invention.

In another aspect of the present invention, if a cyst warrants marking, such as for future examination, a clip could be immediately delivered into the inside of the cyst, while the aspiration needle remains in place. The aspiration needle thus also functions as the shaft of a delivery device.

Furthermore, the device is not limited to use only for evacuated cysts but also could be used for marking solid masses.

As also discussed further herein, preferred clips should be small enough to fit through any typical coaxial needle that would be used for breast biopsy. This will require that the delivery tube preferably be of a thin-wall construction over a portion of or all of its length (and optionally coated over at least a portion of its exterior or interior surface) so the resulting thickness of the delivery tube for the clip and therefore strength of the shape memory of the wire can be maximized. Of course, this device could then be used either with or without a coaxial needle (which also may be coated over at least a portion of its exterior or interior surface).

The skilled artisan will appreciate that among the advantages of the present inventive clip design is that is grabs a relatively large amount of tissue. Another advantage of the present inventive clip is that is does not form a spiral configuration. The proposed clip design is thus highly resistant to any accidental migration.

In use, the present inventive clip design also affords the advantage that, such as using ultrasound guidance, it is possible to place the clip either into the central portion of or next to the mass under consideration for biopsy. It is generally only necessary to see the tip of the needle well and for there to be a positive feel to know that the clip has been deployed.

Biopsies or mass (e.g., breast cyst) aspirations performed in accordance with the present invention can be performed using any suitable size needle (e.g., 10 to 20 gauge, and more preferably 11 to 15 gauge). Clips of the present invention are preferably of a thickness, diameter or other dimension so that they are capable of passing through the needle. For a wire-based clip, the wire chosen is thus preferably of a smaller gauge than the needle, and more preferably a smaller gauge by a factor of at least one half, so that the wire can be folded upon itself, such as about an apex or flattened for placement into the needle or other tube for delivery. The clips can be hollow cored structures, solid structures (e.g., wire) or filled core structures. They may be coated or uncoated. For example, they may have a pharmaceutical agent over some or all of its outer or inner surfaces.

For any of the embodiments of the present invention, a line or other marking may be inscribed onto the surface of the needle and/or needle hub as well as onto the surface of the gripping portion and/or hub of the clip device. The lines will allow precise alignment of the needle and device to indicate proper assembly. This would therefore provide confirmation that the opening of the clip device is aligned with the opening of the needle.

Kits may be provided and used in accordance with the present invention. Examples of components suitable for inclusion in such a kit include, without limitation, one or more of needles, sutures, syringe, anesthetic, sterile wipes, a sharps disposal container, gloves or the like.

The devices of the present invention preferably will be packaged in a sealed sterile container. The container may include, a transparent wall, an opaque wall or a combination thereof. The devices are preferably used only once and are disposable. In one embodiment, the devices are fabricated with plastic or metal components that can be recycled.

The present invention also contemplates methods of using the devices disclosed herein. For example, in one embodiment, a method is contemplated for performing a biopsy using a clip of the present invention. In another embodiment, the delivery device herein is used for delivering a clip, such as during a biopsy. The methods discussed in the Background section herein are particularly suitable for use of the devices of the present invention. Thus, the devices of the present invention may be used for percutaneous biopsies, ultrasound guided biopsies or a combination thereof. Kits may be provided and used in performing such procedures.

The present invention is particularly suitable for mammographic analysis of humans, and particularly female humans, but it is not limited thereto. Without limitation, it can be used for analysis of other human body parts, or for analysis of mammals or other animals other than humans.

References to the use of a Mammotome® device herein are not intended to foreclose the use of other like devices for performing one or more of the tissue removal, marking or other functions performed by the Mammotome® device. Accordingly the present invention also contemplates substituting for the Mammotome® device that is described other such devices, which preferably will have an elongated delivery tube or like structure having chamber through which a clip according to the present invention is advanced, such as by a push rod or the like.

Though a preferred ejection direction is shown in the accompanying drawings for the deployment of the clips, it is possible to deploy the clips so the apex is the leading portion of the clip.

Further, in addition to the discussion of the clip contained herein, there may be greater than two straight or arcuate portions for the clips. The straight and arcuate portions can be of the same or different size or shape relative to each other. They may be formed of a single component (e.g., a single wire) or plural components (e.g., plural wires (2, 3 or more wires) such as might result in a structure as in FIGS. 4C, 4D, 5A and others illustrated). The portions need not be arcuate alone or straight alone, but may be straight, or a combination of straight and arcuate. In another embodiment, as seen in FIGS. 5A, 5B and 6B-6D, the clip may be "X" shaped or may have orthogonally disposed arms. The clips alternatively may be "N" shaped, arrows, arcs, tetragonal, or any of a number of different shapes. Combinations of any of the shapes identified may be employed also. Clips may also include one or a plurality of barbed ends (such as is illustrated by various of the examples provided in FIG. 16). When two or more wires are employed they may be configured relative to each other for deployment in a single common plane or over plural different planes. Though larger clips are also possible, when deployed, preferred clips are smaller than about 1 cm in its largest dimension (e.g., length, diameter, etc.), and more preferably, they are on the order of about 5 mm in its largest dimension.

As illustrated in FIGS. 5A-5C, clips herein may be configured to lie in a single plane (FIG. 5B) or include one or more portions that lie in a plurality of different planes, as in FIG. 5C.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. For example, the employment of a luer lock may be used in the various embodiments shown to connect components, omitted or substituted with an alternative connector, a guide ramp employed or omitted, side holes might be substituted for end holes, or end holes substituted for side holes, even though such feature might not be shown in the accompanying drawings. Bevel shapes can vary from those depicted. The use of different material combinations than those shown might also be appropriate, such as the substitution of metal for plastic, or plastic for metal. It will also be appreciated from the above that the fabrication of the unique structures herein and the operation thereof also constitute methods in accordance with the present invention.

The preferred embodiment of the present invention has been disclosed. A person of ordinary skill in the art would realize however, that certain modifications would come within the teachings of this invention. Therefore, the following claims should be studied to determine the true scope and content of the invention.

What is claimed is:

1. An improved clip for marking breast tissue of a biopsy site or the site of an aspirated cyst during a radiographic analysis, the clip extending along an axis between a first end and a second end and comprising a metal structure consisting essentially of:
   a first arc segment having a first end located at the first end of the clip and a second end located at the second end of the clip;
   a second arc segment having a first end located at the first end of the clip and a second end located at the second end of the clip, the second arc segment being coplanar with the first arc segment; and
   an apex disposed along the clip axis defining where the first and second arc segments adjoin and converge,
   wherein, after being driven through an exit opening of a delivery tube of a delivery device, the metal structure penetrates breast tissue, wherein the metal structure is configured so that
      (i) it resides entirely within the delivery tube prior to being driven through the exit opening,
      (ii) it deploys through the exit opening of the delivery device, and
      (iii) in both an original pre-deployment state and a post-deployment state:
         the first ends of the first and second arc segments project in a direction outward relative to the clip axis, and the second ends of the first and second arc segments project in a direction outward relative to the clip axis, while residing within the delivery tube,
         the first ends of the first and second arc segments project in a direction generally away from the second ends of the first and second arc segments;
      (iv) while it resides within the delivery tube prior to being driven through the exit opening, and after being driven through the exit opening the first and second arc segments are arcuate; and
      (v) the first ends and the second ends of the first and second arc segments penetrate breast tissue after being driven through the exit opening of the delivery tube, the clip does not form a spiral configuration, and thereby substantially prevent migration of the deployed clip within the breast.

2. The clip of claim 1, wherein the clip further includes a coating.

3. The clip of claim 2, wherein the exit opening is located on the side of the delivery device and the clip is configured to deploy along a ramp.

4. The clip of claim 2, wherein the clip is configured so that while within the delivery tube the clip contacts an inner wall of the delivery tube.

5. The clip of claim 2, wherein the clip is in the order of about 5 mm in its largest dimension.

6. The clip of claim 2, wherein the structure of the clip is generally two back to back C shaped segments while in the original pre-deployment state and post-deployment state.

7. The clip of claim 2, wherein the clip is configured to be directed out of the tube opening along a ramp, and the ramp is aligned with the exit opening such that the tube does not cover the ramp.

8. The clip of claim 1, wherein the exit opening is located on the side of the delivery device and the clip is configured to deploy along a ramp.

9. The clip of claim 8, wherein the clip is configured so that while within the delivery tube the clip contacts an inner wall of the delivery tube.

10. The clip of claim 8, wherein the clip is in the order of about 5 mm in its largest dimension.

11. The clip of claim 8, wherein the structure of the clip is generally two back to back C shaped segments while in the original pre-deployment state and post-deployment state.

12. The clip of claim 8, wherein the ramp is configured to be aligned with the exit opening such that the tube does not cover the ramp.

13. The clip of claim 1, wherein the clip is configured so that while within the delivery tube the clip contacts an inner wall of the delivery tube.

14. The clip of claim 13, wherein the clip is in the order of about 5 mm in its largest dimension.

15. The clip of claim 13, wherein the structure of the clip is generally two back to back C shaped segments while in the original pre-deployment state and post-deployment state.

16. The clip of claim 13, wherein the clip is configured to be directed out of the tube opening along a ramp, and the ramp is aligned with the exit opening such that the tube does not cover the ramp.

17. The clip of claim 1, wherein the clip is in the order of about 5 mm in its largest dimension.

18. The clip of claim 17, wherein the structure of the clip is generally two back to back C shaped segments while in original pre-deployment state and post-deployment state.

19. The clip of claim 18, wherein the clip is configured to be directed out of the tube opening along a ramp, and the ramp is aligned with the exit opening such that the tube does not cover the ramp.

20. The clip of claim 1, wherein the structure of the clip is generally two back to back C shaped segments.

* * * * *